(12) United States Patent
Wilk et al.

(10) Patent No.: US 7,736,327 B2
(45) Date of Patent: *Jun. 15, 2010

(54) METHODS AND CONDUITS FOR FLOWING BLOOD FROM A HEART CHAMBER TO A BLOOD VESSEL

(75) Inventors: Peter J. Wilk, New York, NY (US); David Y. Phelps, Louisville, KY (US); Scott J. Wolf, Minneapolis, MN (US)

(73) Assignee: JenaValve Technology, Inc., Wilmington, DE (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/149,901

(22) Filed: May 9, 2008

(65) Prior Publication Data

US 2008/0262602 A1  Oct. 23, 2008

Related U.S. Application Data

(60) Division of application No. 10/928,190, filed on Aug. 30, 2004, now Pat. No. 7,704,222, which is a continuation of application No. 09/828,794, filed on Apr. 10, 2001, now Pat. No. 6,881,199, which is a continuation of application No. 09/369,061, filed on Aug. 4, 1999, now Pat. No. 6,254,564.

(60) Provisional application No. 60/099,719, filed on Sep. 10, 1998.

(51) Int. Cl.
*A61M 5/00* (2006.01)
*A61B 17/08* (2006.01)
*A61F 2/06* (2006.01)
*A61F 2/04* (2006.01)

(52) U.S. Cl. .................. 604/9; 606/153; 623/1.24; 623/23.68

(58) Field of Classification Search ....... 604/4.01–6.16, 604/8, 9, 96.01; 623/1.1–1.26, 2.1, 2.12–2.19; 606/153

See application file for complete search history.

(56) References Cited

U.S. PATENT DOCUMENTS 3,657,744 A    4/1972   Ersek (Continued)

FOREIGN PATENT DOCUMENTS

AU    2001281277 B2    11/2001

(Continued)

OTHER PUBLICATIONS

Aortenklappenbioprothese erfolgreich in der Entwicklung, (1 page) May 16, 2003.

(Continued)

*Primary Examiner*—Leslie R. Deak
*Assistant Examiner*—Philip R Wiest
(74) *Attorney, Agent, or Firm*—Finnegan, Henderson, Farabow, Garrett & Dunner, L.L.P.

(57) ABSTRACT

Disclosed is a conduit that provides a bypass around an occlusion or stenosis in a coronary artery. The conduit is a tube adapted to be positioned in the heart wall to provide a passage for blood to flow between a heart chamber and a coronary artery, at a site distal to the occlusion or stenosis. The conduit has a section of blood vessel attached to its interior lumen which preferably includes at least one naturally occurring one-way valve positioned therein. The valve prevents the backflow of blood from the coronary artery into the heart chamber.

48 Claims, 2 Drawing Sheets

U.S. PATENT DOCUMENTS

| | | |
|---|---|---|
| 4,056,854 A | 11/1977 | Boretos et al. |
| 4,106,129 A | 8/1978 | Carpentier et al. |
| 4,118,806 A | 10/1978 | Porier et al. |
| 4,263,680 A | 4/1981 | Reul et al. |
| 4,350,492 A | 9/1982 | Wright et al. |
| 4,388,735 A | 6/1983 | Ionescu et al. |
| 4,441,215 A | 4/1984 | Kaster |
| 4,546,499 A | 10/1985 | Possis et al. |
| 4,562,597 A | 1/1986 | Possis et al. |
| 4,733,665 A | 3/1988 | Palmaz |
| 4,769,029 A | 9/1988 | Patel |
| 4,878,906 A | 11/1989 | Lindemann et al. |
| 4,953,553 A | 9/1990 | Tremulis |
| 5,002,566 A | 3/1991 | Carpentier et al. |
| 5,061,277 A | 10/1991 | Carpentier et al. |
| 5,089,015 A | 2/1992 | Ross |
| 5,094,661 A | 3/1992 | Levy et al. |
| 5,104,407 A | 4/1992 | Lam et al. |
| 5,147,388 A | 9/1992 | Yamazaki |
| 5,193,546 A | 3/1993 | Shaknovich |
| 5,197,979 A | 3/1993 | Quintero et al. |
| 5,258,008 A | 11/1993 | Wilk |
| 5,275,580 A | 1/1994 | Yamazaki |
| 5,279,612 A | 1/1994 | Eberhardt |
| 5,287,861 A | 2/1994 | Wilk |
| 5,330,486 A | 7/1994 | Wilk |
| 5,332,402 A | 7/1994 | Teitelbaum |
| 5,336,258 A | 8/1994 | Quintero et al. |
| 5,344,426 A | 9/1994 | Lau et al. |
| 5,352,240 A | 10/1994 | Ross |
| 5,368,608 A | 11/1994 | Levy et al. |
| 5,389,096 A | 2/1995 | Aita et al. |
| 5,409,019 A | 4/1995 | Wilk |
| 5,411,552 A | 5/1995 | Andersen et al. |
| 5,429,144 A | 7/1995 | Wilk |
| 5,456,712 A | 10/1995 | Maginot |
| 5,456,713 A | 10/1995 | Chuter |
| 5,470,320 A | 11/1995 | Tiefenbrun et al. |
| 5,500,014 A | 3/1996 | Quijano et al. |
| 5,509,930 A | 4/1996 | Love |
| 5,527,337 A | 6/1996 | Stack et al. |
| 5,545,214 A | 8/1996 | Stevens |
| 5,549,666 A | 8/1996 | Hata et al. |
| 5,554,119 A | 9/1996 | Harrison et al. |
| 5,554,185 A | 9/1996 | Block et al. |
| 5,571,167 A | 11/1996 | Maginot |
| 5,571,215 A | 11/1996 | Sterman et al. |
| 5,593,434 A | 1/1997 | Williams |
| 5,595,571 A | 1/1997 | Jaffe et al. |
| 5,609,626 A | 3/1997 | Quijano et al. |
| 5,613,982 A | 3/1997 | Goldstein |
| 5,618,299 A | 4/1997 | Khosravi et al. |
| 5,632,778 A | 5/1997 | Goldstein |
| 5,655,548 A | 8/1997 | Nelson et al. |
| 5,662,124 A | 9/1997 | Wilk |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,733,267 A | 3/1998 | Del Toro |
| 5,746,775 A | 5/1998 | Levy et al. |
| 5,755,682 A | 5/1998 | Knudson et al. |
| 5,755,777 A | 5/1998 | Chuter |
| 5,758,663 A | 6/1998 | Wilk et al. |
| 5,795,331 A | 8/1998 | Cragg et al. |
| 5,797,946 A | 8/1998 | Chin |
| 5,807,384 A | 9/1998 | Mueller |
| 5,810,836 A | 9/1998 | Hussein et al. |
| 5,824,038 A | 10/1998 | Wall |
| 5,824,041 A | 10/1998 | Lenker et al. |
| 5,824,071 A | 10/1998 | Nelson et al. |
| 5,824,080 A | 10/1998 | Lamuraglia |
| 5,830,222 A | 11/1998 | Makower |
| 5,840,081 A | 11/1998 | Andersen et al. |
| 5,841,382 A | 11/1998 | Walden et al. |
| 5,843,181 A | 12/1998 | Jaffe et al. |
| 5,865,723 A | 2/1999 | Love |
| 5,876,373 A | 3/1999 | Giba et al. |
| 5,876,434 A | 3/1999 | Flomenblit et al. |
| 5,878,751 A | 3/1999 | Hussein et al. |
| 5,880,242 A | 3/1999 | Hu et al. |
| 5,885,259 A | 3/1999 | Berg |
| 5,899,936 A | 5/1999 | Goldstein |
| 5,908,028 A | 6/1999 | Wilk |
| 5,908,029 A | 6/1999 | Knudson et al. |
| 5,916,193 A * | 6/1999 | Stevens et al. ............... 604/509 |
| 5,922,022 A | 7/1999 | Nash et al. |
| 5,925,012 A | 7/1999 | Murphy-Chutorian et al. |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,944,019 A | 8/1999 | Knudson et al. |
| 5,104,407 A | 9/1999 | Lam et al. |
| 5,968,064 A | 10/1999 | Selmon et al. |
| 5,971,993 A | 10/1999 | Hussein et al. |
| 5,976,155 A | 11/1999 | Foreman et al. |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,533 A | 11/1999 | Holman |
| 5,980,548 A | 11/1999 | Evans et al. |
| 5,984,956 A | 11/1999 | Tweden et al. |
| 5,989,276 A | 11/1999 | Houser et al. |
| 5,989,287 A | 11/1999 | Yang et al. |
| 5,993,481 A | 11/1999 | Marcade et al. |
| 5,997,525 A | 12/1999 | March et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 5,061,277 A | 2/2000 | Carpentier et al. |
| 6,026,814 A | 2/2000 | LaFontaine et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,581 A | 3/2000 | Ryan et al. |
| 6,045,565 A | 4/2000 | Ellis et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,077,297 A | 6/2000 | Robinson et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |

| Patent No. | Date | Inventor |
|---|---|---|
| 6,093,530 A | 7/2000 | McIlroy et al. |
| 6,102,941 A | 8/2000 | Tweden et al. |
| 6,102,944 A | 8/2000 | Huynh et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,123,682 A | 9/2000 | Knudson et al. |
| 6,126,649 A | 10/2000 | VanTassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,139,541 A | 10/2000 | Vanney et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,168,614 B1 | 1/2001 | Andersen et al. |
| 6,171,251 B1 | 1/2001 | Mueller et al. |
| 6,177,514 B1 | 1/2001 | Pathak et al. |
| 6,182,668 B1 | 2/2001 | Tweden et al. |
| 6,183,481 B1 | 2/2001 | Lee et al. |
| 6,186,972 B1 | 2/2001 | Nelson et al. |
| 6,190,353 B1 | 2/2001 | Makower et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,741 B1 | 6/2001 | Duhaylongsod et al. |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,636 B1 | 7/2001 | Peredo |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,338 B1 | 9/2001 | Sarnowski et al. |
| 6,290,709 B1 | 9/2001 | Ellis et al. |
| 6,290,728 B1 * | 9/2001 | Phelps et al. ............... 623/23.7 |
| 6,302,875 B1 | 10/2001 | Makower et al. |
| 6,302,892 B1 | 10/2001 | Wilk |
| 6,322,548 B1 | 11/2001 | Payne et al. |
| 6,330,884 B1 | 12/2001 | Kim |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,248 B1 | 2/2002 | Knudson et al. |
| 6,350,278 B1 | 2/2002 | Lenker et al. |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,379,740 B1 | 4/2002 | Rinaldi et al. |
| 6,387,119 B2 | 5/2002 | Wolf et al. |
| 6,390,098 B1 | 5/2002 | LaFontaine et al. |
| 6,391,538 B1 | 5/2002 | Vyavahare et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,471,723 B1 | 10/2002 | Ashworth et al. |
| 6,475,226 B1 | 11/2002 | Belef et al. |
| 6,475,244 B2 | 11/2002 | Herweck et al. |
| 6,478,819 B2 | 11/2002 | Moe |
| 6,482,220 B1 | 11/2002 | Mueller |
| 6,491,689 B1 | 12/2002 | Ellis et al. |
| 6,491,707 B2 | 12/2002 | Makower et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,521,179 B1 | 2/2003 | Girardot et al. |
| 6,524,323 B1 | 2/2003 | Nash et al. |
| 6,540,782 B1 | 4/2003 | Snyders |
| 6,544,230 B1 | 4/2003 | Flaherty |
| 6,558,417 B2 | 5/2003 | Peredo |
| 6,558,418 B2 | 5/2003 | Carpentier et al. |
| 6,559,132 B1 | 5/2003 | Holmer |
| 6,561,998 B1 | 5/2003 | Roth et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,572,642 B2 | 6/2003 | Rinaldi et al. |
| 6,575,168 B2 | 6/2003 | LaFontaine et al. |
| 6,579,311 B1 | 6/2003 | Makower |

| Patent No. | Date | Inventor |
|---|---|---|
| 6,582,444 B2 | 6/2003 | Wilk |
| 6,582,462 B1 | 6/2003 | Andersen et al. |
| 6,585,766 B1 | 7/2003 | Huynh et al. |
| 6,599,304 B1 | 7/2003 | Selmon et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,632,470 B2 | 10/2003 | Morra et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,669,709 B1 | 12/2003 | Cohn et al. |
| 6,682,559 B2 | 1/2004 | Myers et al. |
| 6,685,648 B2 | 2/2004 | Flaherty et al. |
| 6,694,983 B2 | 2/2004 | Wolf et al. |
| 6,701,932 B2 | 3/2004 | Knudson et al. |
| 6,709,425 B2 | 3/2004 | Gambale et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,730,118 B2 | 5/2004 | Spenser et al. |
| 6,736,845 B2 | 5/2004 | Marquez et al. |
| 6,746,464 B1 | 6/2004 | Makower |
| 6,767,362 B2 | 7/2004 | Schreck |
| 6,774,278 B1 | 8/2004 | Ragheb et al. |
| 6,786,929 B2 | 9/2004 | Gambale et al. |
| 6,790,230 B2 | 9/2004 | Beyersdorf et al. |
| 6,802,858 B2 | 10/2004 | Gambale et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,568 B1 | 12/2004 | Kesten et al. |
| 6,830,584 B1 | 12/2004 | Seguin |
| 6,854,467 B2 | 2/2005 | Boekstegers |
| 6,861,211 B2 | 3/2005 | Levy et al. |
| 6,863,684 B2 | 3/2005 | Kim et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,913,021 B2 | 7/2005 | Knudson et al. |
| 6,916,304 B2 | 7/2005 | Eno et al. |
| 6,926,690 B2 | 8/2005 | Renati |
| 6,929,009 B2 * | 8/2005 | Makower et al. ............ 128/898 |
| 6,929,011 B2 | 8/2005 | Knudson et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,953,481 B2 | 10/2005 | Phelps et al. |
| 6,955,681 B2 | 10/2005 | Evans et al. |
| 6,964,652 B2 | 11/2005 | Guiles et al. |
| 6,974,474 B2 | 12/2005 | Pavcnik et al. |
| 6,976,990 B2 | 12/2005 | Mowry |
| 6,986,784 B1 | 1/2006 | Weiser et al. |
| 7,008,397 B2 | 3/2006 | Tweden et al. |
| 7,011,095 B2 | 3/2006 | Wolf et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck |
| 7,141,064 B2 | 11/2006 | Scott et al. |
| 7,163,556 B2 | 1/2007 | Xie et al. |
| 7,189,259 B2 | 3/2007 | Simionescu et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,473,275 B2 | 1/2009 | Marquez |
| 2001/0000041 A1 | 3/2001 | Selmon et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0011187 A1 | 8/2001 | Pavcnik et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0039450 A1 | 11/2001 | Pavcnik et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0032481 A1 | 3/2002 | Gabbay |
| 2002/0045928 A1 | 4/2002 | Boekstegers |
| 2002/0049486 A1 | 4/2002 | Knudson et al. |
| 2002/0055775 A1 | 5/2002 | Carpentier et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0077566 A1 | 6/2002 | Laroya et al. |
| 2002/0077654 A1 | 6/2002 | Javier, Jr. et al. |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095206 A1 | 7/2002 | Addonizio et al. |
| 2002/0100484 A1 | 8/2002 | Hall et al. |
| 2002/0111672 A1 | 8/2002 | Kim et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0133226 A1 | 9/2002 | Marquez et al. |
| 2002/0138087 A1 | 9/2002 | Shennib et al. |

| | | | | | | |
|---|---|---|---|---|---|---|
| 2002/0143285 A1 | 10/2002 | Eno et al. | | 2004/0133225 A1 | 7/2004 | Makower |
| 2002/0143289 A1 | 10/2002 | Ellis et al. | | 2004/0147868 A1 | 7/2004 | Bardsley et al. |
| 2002/0144696 A1 | 10/2002 | Sharkawy et al. | | 2004/0147869 A1 | 7/2004 | Wolf et al. |
| 2002/0161383 A1 | 10/2002 | Akin et al. | | 2004/0148018 A1 | 7/2004 | Carpentier et al. |
| 2002/0161424 A1 | 10/2002 | Rapacki et al. | | 2004/0153145 A1 | 8/2004 | Simionescu et al. |
| 2002/0165479 A1 | 11/2002 | Wilk | | 2004/0158143 A1 | 8/2004 | Flaherty et al. |
| 2002/0165606 A1 | 11/2002 | Wolf et al. | | 2004/0167444 A1 | 8/2004 | Laroya et al. |
| 2002/0179098 A1 | 12/2002 | Makower et al. | | 2004/0168691 A1 | 9/2004 | Sharkawy et al. |
| 2002/0183716 A1 | 12/2002 | Herweck et al. | | 2004/0186507 A1 | 9/2004 | Hall et al. |
| 2002/0193782 A1 | 12/2002 | Ellis et al. | | 2004/0186557 A1 | 9/2004 | Gambale et al. |
| 2002/0198594 A1 | 12/2002 | Schreck et al. | | 2004/0186558 A1 | 9/2004 | Pavcnik et al. |
| 2003/0018379 A1 | 1/2003 | Knudson et al. | | 2004/0186563 A1 | 9/2004 | Lobbi |
| 2003/0027332 A1 | 2/2003 | Lafrance et al. | | 2004/0186565 A1 | 9/2004 | Schreck |
| 2003/0036795 A1 | 2/2003 | Andersen et al. | | 2004/0186587 A1 | 9/2004 | Ahern |
| 2003/0040792 A1 | 2/2003 | Gabbay | | 2004/0193244 A1 | 9/2004 | Hartley et al. |
| 2003/0044315 A1 | 3/2003 | Boekstegers | | 2004/0210190 A1 | 10/2004 | Kohler et al. |
| 2003/0045828 A1 | 3/2003 | Wilk | | 2004/0210301 A1 | 10/2004 | Obermiller et al. |
| 2003/0050694 A1 | 3/2003 | Yang et al. | | 2004/0210304 A1 | 10/2004 | Seguin et al. |
| 2003/0055371 A1 | 3/2003 | Wolf et al. | | 2004/0219180 A1 | 11/2004 | Gambale et al. |
| 2003/0055495 A1 | 3/2003 | Pease et al. | | 2004/0220598 A1 | 11/2004 | Bolduc et al. |
| 2003/0065386 A1 | 4/2003 | Weadock | | 2004/0225355 A1 | 11/2004 | Stevens |
| 2003/0073973 A1 | 4/2003 | Evans et al. | | 2004/0236418 A1 | 11/2004 | Stevens |
| 2003/0078561 A1 | 4/2003 | Gambale et al. | | 2004/0260389 A1 | 12/2004 | Case et al. |
| 2003/0100920 A1 | 5/2003 | Akin et al. | | 2005/0004505 A1 | 1/2005 | Phelps et al. |
| 2003/0105514 A1 | 6/2003 | Phelps et al. | | 2005/0004558 A1 | 1/2005 | Gambale et al. |
| 2003/0114913 A1 | 6/2003 | Spenser et al. | | 2005/0004648 A1 | 1/2005 | Boekstegers |
| 2003/0120195 A1 | 6/2003 | Milo et al. | | 2005/0009000 A1 | 1/2005 | Wilhelm et al. |
| 2003/0125795 A1 | 7/2003 | Pavcnik et al. | | 2005/0033220 A1 | 2/2005 | Wilk et al. |
| 2003/0139796 A1 | 7/2003 | Sequin et al. | | 2005/0033398 A1 | 2/2005 | Seguin |
| 2003/0139803 A1 | 7/2003 | Sequin et al. | | 2005/0043781 A1 | 2/2005 | Foley |
| 2003/0149474 A1 | 8/2003 | Becker | | 2005/0043790 A1 | 2/2005 | Seguin |
| 2003/0153974 A1 | 8/2003 | Spenser et al. | | 2005/0049692 A1 | 3/2005 | Numamoto et al. |
| 2003/0158573 A1 | 8/2003 | Gittings et al. | | 2005/0075725 A1 | 4/2005 | Rowe |
| 2003/0163198 A1 | 8/2003 | Morra et al. | | 2005/0075776 A1 | 4/2005 | Cho |
| 2003/0181938 A1 | 9/2003 | Roth et al. | | 2005/0096726 A1 | 5/2005 | Sequin et al. |
| 2003/0191449 A1 | 10/2003 | Nash et al. | | 2005/0096736 A1 | 5/2005 | Osse et al. |
| 2003/0195457 A1 | 10/2003 | LaFontaine et al. | | 2005/0098547 A1 | 5/2005 | Cali et al. |
| 2003/0195458 A1 | 10/2003 | Phelps et al. | | 2005/0101903 A1 | 5/2005 | Kohler et al. |
| 2003/0195620 A1 | 10/2003 | Huynh et al. | | 2005/0101904 A1 | 5/2005 | Wilk |
| 2003/0204160 A1 | 10/2003 | Kamm et al. | | 2005/0113910 A1 | 5/2005 | Paniagua et al. |
| 2003/0212413 A1 | 11/2003 | Wilk | | 2005/0119728 A1 | 6/2005 | Sarac |
| 2003/0216678 A1 | 11/2003 | March et al. | | 2005/0119736 A1 | 6/2005 | Zilla et al. |
| 2003/0216679 A1 | 11/2003 | Wolf et al. | | 2005/0137687 A1 | 6/2005 | Salahieh et al. |
| 2003/0220661 A1 | 11/2003 | Mowry et al. | | 2005/0137688 A1 | 6/2005 | Salahieh et al. |
| 2003/0229366 A1 | 12/2003 | Reggie et al. | | 2005/0137690 A1 | 6/2005 | Salahieh et al. |
| 2003/0236542 A1 | 12/2003 | Makower | | 2005/0137697 A1 | 6/2005 | Salahieh et al. |
| 2003/0236570 A1 | 12/2003 | Cook et al. | | 2005/0137698 A1 | 6/2005 | Salahieh et al. |
| 2004/0006298 A1 | 1/2004 | Wilk | | 2005/0137702 A1 | 6/2005 | Haug et al. |
| 2004/0006380 A1 | 1/2004 | Buck et al. | | 2005/0143804 A1 | 6/2005 | Haverkost |
| 2004/0015225 A1 | 1/2004 | Kim et al. | | 2005/0143807 A1 | 6/2005 | Pavcnik et al. |
| 2004/0019348 A1 | 1/2004 | Stevens et al. | | 2005/0149166 A1 | 7/2005 | Schaeffer et al. |
| 2004/0037946 A1 | 2/2004 | Morra et al. | | 2005/0150775 A1 | 7/2005 | Zhang et al. |
| 2004/0039436 A1 | 2/2004 | Spenser et al. | | 2005/0159726 A1 | 7/2005 | Evans et al. |
| 2004/0044392 A1 | 3/2004 | Von Oepen | | 2005/0171597 A1 | 8/2005 | Boatman et al. |
| 2004/0049262 A1 | 3/2004 | Obermiller et al. | | 2005/0171598 A1 | 8/2005 | Schaeffer |
| 2004/0058097 A1 | 3/2004 | Weder | | 2005/0192665 A1 | 9/2005 | Spenser et al. |
| 2004/0059280 A1 | 3/2004 | Makower et al. | | 2005/0197695 A1 | 9/2005 | Stacchino et al. |
| 2004/0073157 A1 | 4/2004 | Knudson et al. | | 2005/0214342 A1 | 9/2005 | Tweden et al. |
| 2004/0073238 A1 | 4/2004 | Makower | | 2005/0222668 A1 | 10/2005 | Schaeffer et al. |
| 2004/0073289 A1 | 4/2004 | Hartley | | 2005/0228334 A1 | 10/2005 | Knudson et al. |
| 2004/0077987 A1 | 4/2004 | Rapacki et al. | | 2005/0234546 A1 | 10/2005 | Nugent et al. |
| 2004/0077988 A1 | 4/2004 | Tweden et al. | | 2005/0267560 A1 | 12/2005 | Bates |
| 2004/0077990 A1 | 4/2004 | Knudson et al. | | 2005/0288685 A1 | 12/2005 | Guiles et al. |
| 2004/0078950 A1 | 4/2004 | Schreck et al. | | 2006/0009842 A1 | 1/2006 | Huynh et al. |
| 2004/0088042 A1 | 5/2004 | Kim et al. | | 2006/0025857 A1 | 2/2006 | Bergheim et al. |
| 2004/0106931 A1 | 6/2004 | Guiles et al. | | 2006/0041218 A1 | 2/2006 | Phelps et al. |
| 2004/0113306 A1 | 6/2004 | Rapacki et al. | | 2006/0047343 A1 | 3/2006 | Oviatt et al. |
| 2004/0117004 A1 | 6/2004 | Osborne et al. | | 2006/0052736 A1 | 3/2006 | Tweden et al. |
| 2004/0117009 A1 | 6/2004 | Cali et al. | | 2006/0058864 A1 | 3/2006 | Schaeffer et al. |
| 2004/0118415 A1 | 6/2004 | Hall et al. | | 2006/0111770 A1 | 5/2006 | Pavcnik et al. |
| 2004/0122318 A1 | 6/2004 | Flaherty et al. | | 2006/0142846 A1 | 6/2006 | Pavcnik et al. |
| 2004/0122347 A1 | 6/2004 | Knudson et al. | | 2006/0149360 A1 | 7/2006 | Schwammenthal et al. |
| 2004/0133154 A1 | 7/2004 | Flaherty et al. | | 2006/0167543 A1 | 7/2006 | Bailey et al. |

| Publication No. | Date | Name | Country | Number | Date |
|---|---|---|---|---|---|
| 2006/0193885 A1 | 8/2006 | Neethling et al. | CA | 2457755 A1 | 2/2003 |
| 2006/0210597 A1 | 9/2006 | Hiles | DE | 28 15 756 A1 | 10/1979 |
| 2006/0229718 A1 | 10/2006 | Marquez | DE | 195 46 692 A1 | 6/1997 |
| 2006/0229719 A1 | 10/2006 | Marquez et al. | DE | 101 21 210 A1 | 11/2002 |
| 2006/0246584 A1 | 11/2006 | Covelli | DE | 195 46 692 C2 | 11/2002 |
| 2006/0259134 A1 | 11/2006 | Schwammenthal et al. | EP | 0084395 A1 | 7/1983 |
| 2006/0259136 A1 | 11/2006 | Nguyen et al. | EP | 0458877 | 8/1990 |
| 2006/0265056 A1 | 11/2006 | Nguyen et al. | EP | 0402036 B1 | 12/1990 |
| 2006/0287717 A1 | 12/2006 | Rowe et al. | EP | 0402176 B1 | 12/1990 |
| 2006/0287719 A1 | 12/2006 | Rowe et al. | EP | 0458877 B1 | 4/1991 |
| 2006/0290027 A1 | 12/2006 | O'Connor et al. | EP | 0515324 A1 | 11/1992 |
| 2006/0293745 A1 | 12/2006 | Carpentier et al. | EP | 0547135 B1 | 6/1993 |
| 2007/0005131 A1 | 1/2007 | Taylor | EP | 0871414 | 9/1995 |
| 2007/0005132 A1 | 1/2007 | Simionescu et al. | EP | 0 592 410 B1 | 10/1995 |
| 2007/0020248 A1 | 1/2007 | Everaerts et al. | EP | 0756498 | 10/1995 |
| 2007/0021826 A1 | 1/2007 | Case et al. | EP | 0 592 410 A1 | 11/1995 |
| 2007/0027535 A1 | 2/2007 | Purdy, Jr. et al. | EP | 0786970 | 5/1996 |
| 2007/0038291 A1 | 2/2007 | Case et al. | EP | 0 732 088 A2 | 9/1996 |
| 2007/0038295 A1 | 2/2007 | Case et al. | EP | 0729364 B1 | 9/1996 |
| 2007/0043435 A1 | 2/2007 | Seguin et al. | EP | 0756498 B1 | 5/1997 |
| 2007/0050014 A1 | 3/2007 | Johnson | EP | 0778775 B1 | 6/1997 |
| 2007/0088431 A1 | 4/2007 | Bourang et al. | EP | 0786970 A0 | 8/1997 |
| 2007/0093887 A1 | 4/2007 | Case et al. | EP | 0 792 624 A1 | 9/1997 |
| 2007/0100435 A1 | 5/2007 | Case et al. | EP | 0888142 | 9/1997 |
| 2007/0112422 A1 | 5/2007 | Dehdashtian | EP | 0 797 957 A1 | 10/1997 |
| 2007/0123700 A1 | 5/2007 | Ueda et al. | EP | 0 797 958 A1 | 10/1997 |
| 2007/0123979 A1 | 5/2007 | Perier et al. | EP | 0 799 604 A1 | 10/1997 |
| 2007/0162103 A1 | 7/2007 | Case et al. | EP | 0 801 928 A1 | 10/1997 |
| 2007/0173932 A1 | 7/2007 | Cali et al. | EP | 0 815 798 A2 | 1/1998 |
| 2007/0179592 A1 | 8/2007 | Schaeffer | EP | 0 829 239 A1 | 3/1998 |
| 2007/0185565 A1 | 8/2007 | Schwammenthal et al. | EP | 0 836 834 A2 | 4/1998 |
| 2007/0203576 A1 | 8/2007 | Lee et al. | EP | 0 853 921 A2 | 7/1998 |
| 2007/0213813 A1 | 9/2007 | Von Segesser et al. | EP | 0 858 779 A1 | 8/1998 |
| 2007/0239271 A1 | 10/2007 | Nguyen | EP | 0971649 A0 | 10/1998 |
| 2007/0244551 A1 | 10/2007 | Stobie | EP | 0 876 796 A2 | 11/1998 |
| 2007/0260327 A1 | 11/2007 | Case et al. | EP | 0 876 803 A2 | 11/1998 |
| 2007/0288087 A1 | 12/2007 | Fearnot et al. | EP | 0 888 750 A1 | 1/1999 |
| 2008/0004688 A1 | 1/2008 | Spenser et al. | EP | 0 895 752 A1 | 2/1999 |
| 2008/0021546 A1 | 1/2008 | Patz et al. | EP | 0928615 A1 | 7/1999 |
| 2008/0033534 A1 | 2/2008 | Cook et al. | EP | 1051204 | 7/1999 |
| 2008/0065011 A1 | 3/2008 | Marchand et al. | EP | 0 934 728 A2 | 8/1999 |
| 2008/0071361 A1 | 3/2008 | Tuval et al. | EP | 1089676 | 12/1999 |
| 2008/0071362 A1 | 3/2008 | Tuval et al. | EP | 0986348 B1 | 3/2000 |
| 2008/0071363 A1 | 3/2008 | Tuval et al. | EP | 1117446 A0 | 4/2000 |
| 2008/0071366 A1 | 3/2008 | Tuval et al. | EP | 1 020 166 A1 | 7/2000 |
| 2008/0071368 A1 | 3/2008 | Tuval et al. | EP | 1 027 870 A1 | 8/2000 |
| 2008/0071369 A1 | 3/2008 | Tuval et al. | EP | 1 164 976 A0 | 8/2000 |
| 2008/0077236 A1 | 3/2008 | Letac et al. | EP | 1158937 A0 | 9/2000 |
| 2008/0086205 A1 | 4/2008 | Gordy et al. | EP | 1 251 805 B1 | 10/2000 |
| 2008/0097586 A1 | 4/2008 | Pavcnik et al. | EP | 1041942 B1 | 10/2000 |
| 2008/0102439 A1 | 5/2008 | Tian et al. | EP | 1041943 B1 | 10/2000 |
| 2008/0133003 A1 | 6/2008 | Seguin et al. | EP | 1171061 A0 | 10/2000 |
| 2008/0140189 A1 | 6/2008 | Nguyen et al. | EP | 1206179 A0 | 2/2001 |
| 2008/0154355 A1 | 6/2008 | Benichou et al. | EP | 1 097 676 B1 | 5/2001 |
| 2008/0200977 A1 | 8/2008 | Paul et al. | EP | 1 233 731 A0 | 5/2001 |
| 2008/0215143 A1 | 9/2008 | Seguin | EP | 1117446 B1 | 7/2001 |
| 2008/0269878 A1 | 10/2008 | Iobbi | EP | 1 255 510 A0 | 8/2001 |
| 2008/0275549 A1 | 11/2008 | Rowe | EP | 1 166 721 A2 | 1/2002 |
| | | | EP | 1 233 731 B1 | 5/2002 |
| FOREIGN PATENT DOCUMENTS | | | EP | 1 330 213 A0 | 5/2002 |
| | | | EP | 1206179 B1 | 5/2002 |
| AU | 757647 B2 | 2/2003 | EP | 1347785 A0 | 8/2002 |
| AU | 776895 B2 | 9/2004 | EP | 1235537 A0 | 9/2002 |
| AU | 777443 B2 | 10/2004 | EP | 1248655 A0 | 10/2002 |
| AU | 778831 B2 | 12/2004 | EP | 1251804 B1 | 10/2002 |
| AU | 2004231189 A1 | 12/2004 | EP | 1257305 A0 | 11/2002 |
| AU | 2004242527 A1 | 1/2005 | EP | 0 959 815 A1 | 12/2002 |
| CA | 2378589 A1 | 2/2001 | EP | 0 971 649 B1 | 12/2002 |
| CA | 2381192 A1 | 2/2001 | EP | 1395208 A0 | 12/2002 |
| CA | 2385662 A1 | 3/2001 | EP | 1 401 359 A0 | 1/2003 |
| CA | 2407987 A1 | 11/2001 | EP | 1406561 A0 | 1/2003 |
| CA | 2418958 A1 | 2/2002 | EP | 1281357 A2 | 2/2003 |
| CA | 2435962 A1 | 8/2002 | EP | 1408882 A0 | 2/2003 |

| | | | | | | |
|---|---|---|---|---|---|---|
| EP | 1 435 878 A0 | 4/2003 | | WO | WO 96/39964 A1 | 12/1996 |
| EP | 1 435 879 A0 | 4/2003 | | WO | WO 96/39965 A1 | 12/1996 |
| EP | 1 112 097 A1 | 6/2003 | | WO | WO 97/13463 A1 | 4/1997 |
| EP | 1 441 672 A0 | 6/2003 | | WO | WO 97/13471 A1 | 4/1997 |
| EP | 1 017 868 B1 | 9/2003 | | WO | WO 97/27893 A1 | 8/1997 |
| EP | 1354569 A1 | 10/2003 | | WO | WO 97/27897 A1 | 8/1997 |
| EP | 1494616 | 10/2003 | | WO | WO 97/27898 A1 | 8/1997 |
| EP | 1 519 697 A0 | 1/2004 | | WO | WO 97/32551 A1 | 9/1997 |
| EP | 1 539 047 A0 | 4/2004 | | WO | WO-97/32615 | 9/1997 |
| EP | 1551274 A0 | 4/2004 | | WO | WO 97/43961 A1 | 11/1997 |
| EP | 1 560 542 A0 | 5/2004 | | WO | WO 98/03118 A1 | 1/1998 |
| EP | 1414295 A0 | 5/2004 | | WO | WO 98/06356 A1 | 2/1998 |
| EP | 0 954 248 B1 | 9/2004 | | WO | WO 98/08456 | 3/1998 |
| EP | 1 603 493 A0 | 9/2004 | | WO | WO 98/08456 A1 | 3/1998 |
| EP | 1452153 A1 | 9/2004 | | WO | WO 98/10714 A1 | 3/1998 |
| EP | 0987998 | 10/2004 | | WO | WO 98/16161 A1 | 4/1998 |
| EP | 1 087 727 B1 | 11/2004 | | WO | WO 98/24373 A1 | 6/1998 |
| EP | 1 115 452 B1 | 11/2004 | | WO | WO 98/25533 A1 | 6/1998 |
| EP | 1 477 202 A2 | 11/2004 | | WO | WO 98/25549 | 6/1998 |
| EP | 1 107 710 B1 | 12/2004 | | WO | WO 98/38916 A1 | 9/1998 |
| EP | 1 484 081 A1 | 12/2004 | | WO | WO 98/38925 A1 | 9/1998 |
| EP | 1499366 B1 | 1/2005 | | WO | WO 98/38939 A1 | 9/1998 |
| EP | 1 143 879 B1 | 3/2005 | | WO | WO 98/38941 A1 | 9/1998 |
| EP | 1 516 599 A2 | 3/2005 | | WO | WO 98/39038 A1 | 9/1998 |
| EP | 1 663 070 A0 | 3/2005 | | WO | WO-98/43556 | 10/1998 |
| EP | 1 253 875 B1 | 4/2005 | | WO | WO 98/46115 A2 | 10/1998 |
| EP | 1 522 278 A1 | 4/2005 | | WO | WO 98/46119 A1 | 10/1998 |
| EP | 1 667 614 A0 | 4/2005 | | WO | WO-98/46165 | 10/1998 |
| EP | 1 251 803 B1 | 6/2005 | | WO | WO 98/49964 A1 | 11/1998 |
| EP | 1 547 533 A2 | 6/2005 | | WO | WO 98/57590 A1 | 12/1998 |
| EP | 1 702 247 A0 | 7/2005 | | WO | WO 98/57591 A1 | 12/1998 |
| EP | 1 027 013 B1 | 8/2005 | | WO | WO 98/57592 A1 | 12/1998 |
| EP | 1734902 A0 | 8/2005 | | WO | WO 99/07296 A1 | 2/1999 |
| EP | 1 011 523 A1 | 11/2005 | | WO | WO 99/08624 A1 | 2/1999 |
| EP | 1 067 869 B1 | 11/2005 | | WO | WO 99/15220 A1 | 4/1999 |
| EP | 1 600 110 A1 | 11/2005 | | WO | WO 99/17671 A1 | 4/1999 |
| EP | 1 021 141 B1 | 1/2006 | | WO | WO 99/17683 A1 | 4/1999 |
| EP | 1 616 536 A2 | 1/2006 | | WO | WO 99/21490 A1 | 5/1999 |
| EP | 1835948 A0 | 6/2006 | | WO | WO 99/21510 A1 | 5/1999 |
| EP | 1863545 A0 | 9/2006 | | WO | WO 99/22655 A1 | 5/1999 |
| EP | 1893132 A0 | 11/2006 | | WO | WO 99/22658 A1 | 5/1999 |
| EP | 1901681 A0 | 12/2006 | | WO | WO 99/25273 A1 | 5/1999 |
| EP | 1 255 510 B1 | 3/2007 | | WO | WO 99/27985 A1 | 6/1999 |
| EP | 1835948 A0 | 9/2007 | | WO | WO 99/35977 A1 | 7/1999 |
| EP | 1878407 A1 | 1/2008 | | WO | WO 99/35979 A1 | 7/1999 |
| EP | 1 900 343 A2 | 3/2008 | | WO | WO 99/35980 A1 | 7/1999 |
| EP | 2 000 115 A2 | 12/2008 | | WO | WO 99/36000 A1 | 7/1999 |
| FR | 2 432 305 | 2/1980 | | WO | WO 99/36001 | 7/1999 |
| GB | 2 018 950 A | 10/1979 | | WO | WO 99/36001 A1 | 7/1999 |
| GB | 2 316 322 B | 10/1998 | | WO | WO-99/37337 | 7/1999 |
| GB | 2440809 A | 2/2008 | | WO | WO 99/38459 A2 | 8/1999 |
| JP | 54-137896 | 9/1979 | | WO | WO 99/40853 A1 | 8/1999 |
| JP | 4-47576 | 4/1992 | | WO | WO 99/40868 A1 | 8/1999 |
| JP | 4-505866 | 10/1992 | | WO | WO 99/40963 A1 | 8/1999 |
| JP | 8-33715 | 1/1994 | | WO | WO 99/44524 A2 | 9/1999 |
| JP | 6-505187 | 6/1994 | | WO | WO 99/48545 A1 | 9/1999 |
| JP | 7-505803 | 6/1995 | | WO | WO 99/48549 A2 | 9/1999 |
| JP | 10-507673 | 7/1998 | | WO | WO 99/49793 A1 | 10/1999 |
| SE | 7901667 A | 7/1985 | | WO | WO 99/49910 A2 | 10/1999 |
| WO | WO 84/02266 | 6/1984 | | WO | WO 99/51162 A1 | 10/1999 |
| WO | WO-90/09102 | 8/1990 | | WO | WO 99/53863 A1 | 10/1999 |
| WO | WO 90/14804 | 12/1990 | | WO | WO 99/55406 A1 | 11/1999 |
| WO | WO 92/03990 | 3/1992 | | WO | WO 99/60941 A1 | 12/1999 |
| WO | WO 92/14419 | 9/1992 | | WO | WO 99/62430 A1 | 12/1999 |
| WO | WO 93/20757 | 10/1993 | | WO | WO-99/66863 | 12/1999 |
| WO | WO-95/24873 | 9/1995 | | WO | WO 00/09195 A1 | 2/2000 |
| WO | WO-95/28183 | 10/1995 | | WO | WO 00/12029 A1 | 3/2000 |
| WO | WO-95/29713 | 11/1995 | | WO | WO 00/13722 A1 | 3/2000 |
| WO | WO 96/13227 | 5/1996 | | WO | WO 00/15146 A1 | 3/2000 |
| WO | WO-96/13227 | 5/1996 | | WO | WO 00/15147 A1 | 3/2000 |
| WO | WO 96/32972 A1 | 10/1996 | | WO | WO 00/15148 A1 | 3/2000 |
| WO | WO 96/35469 A1 | 11/1996 | | WO | WO 00/15149 A1 | 3/2000 |
| WO | WO 96/39962 A1 | 12/1996 | | WO | WO 00/15275 A2 | 3/2000 |

| | | |
|---|---|---|
| WO | WO 00/16848 A1 | 3/2000 |
| WO | WO 00/18302 A2 | 4/2000 |
| WO | WO 00/18323 A2 | 4/2000 |
| WO | WO 00/18325 A1 | 4/2000 |
| WO | WO 00/18326 A1 | 4/2000 |
| WO | WO 00/18331 A2 | 4/2000 |
| WO | WO-00/18445 | 4/2000 |
| WO | WO 00/18462 A2 | 4/2000 |
| WO | WO 00/21436 A1 | 4/2000 |
| WO | WO 00/21461 A2 | 4/2000 |
| WO | WO 00/21463 A1 | 4/2000 |
| WO | WO 00/24449 A1 | 5/2000 |
| WO | WO 00/25702 A1 | 5/2000 |
| WO | WO 00/33725 A2 | 6/2000 |
| WO | WO 00/35376 A1 | 6/2000 |
| WO | WO 00/36997 A1 | 6/2000 |
| WO | WO 00/41632 A1 | 7/2000 |
| WO | WO 00/41633 A1 | 7/2000 |
| WO | WO 00/43051 A1 | 7/2000 |
| WO | WO 00/45711 A1 | 8/2000 |
| WO | WO 00/45886 A2 | 8/2000 |
| WO | WO 00/47139 | 8/2000 |
| WO | WO 00/47139 A1 | 8/2000 |
| WO | WO 00/49952 A1 | 8/2000 |
| WO | WO 00/49954 A2 | 8/2000 |
| WO | WO 00/49956 A1 | 8/2000 |
| WO | WO-00/53125 | 9/2000 |
| WO | WO 00/54660 A1 | 9/2000 |
| WO | WO 00/54661 A1 | 9/2000 |
| WO | WO 00/56224 A1 | 9/2000 |
| WO | WO 00/56225 A1 | 9/2000 |
| WO | WO 00/56387 A1 | 9/2000 |
| WO | WO-00/62714 | 10/2000 |
| WO | WO 00/66007 A1 | 11/2000 |
| WO | WO 00/66009 A1 | 11/2000 |
| WO | WO 00/66035 A1 | 11/2000 |
| WO | WO 00/69345 A1 | 11/2000 |
| WO | WO 00/69504 A1 | 11/2000 |
| WO | WO 00/71195 A1 | 11/2000 |
| WO | WO 01/08566 A1 | 2/2001 |
| WO | WO 01/08602 A1 | 2/2001 |
| WO | WO-01/10209 A1 | 2/2001 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/54625 A1 | 2/2001 |
| WO | WO 01/17440 A1 | 3/2001 |
| WO | WO 01/17456 A1 | 3/2001 |
| WO | WO 01/35870 A1 | 5/2001 |
| WO | WO-01/41679 A1 | 6/2001 |
| WO | WO 01/49187 A1 | 7/2001 |
| WO | WO-01/51104 A1 | 7/2001 |
| WO | WO-01/58503 A1 | 8/2001 |
| WO | WO 01/82837 A2 | 11/2001 |
| WO | WO 02/11647 A2 | 2/2002 |
| WO | WO 02/36048 A1 | 5/2002 |
| WO | WO-02/058745 A1 | 8/2002 |
| WO | WO 02/060509 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO-03/009785 A1 | 2/2003 |
| WO | WO 03/011195 A2 | 2/2003 |
| WO | WO 03/013239 | 2/2003 |
| WO | WO 03/028592 A1 | 4/2003 |
| WO | WO 03/032870 A1 | 4/2003 |
| WO | WO 03/047468 A1 | 6/2003 |
| WO | WO-03/079928 A2 | 10/2003 |
| WO | WO 03/079932 A2 | 10/2003 |
| WO | WO 03/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO-2004/026117 A2 | 4/2004 |
| WO | WO 2004/026173 A2 | 4/2004 |
| WO | WO 2004/04330 A1 | 5/2004 |
| WO | WO 2004/082527 A2 | 9/2004 |
| WO | WO 2004/096100 A1 | 11/2004 |
| WO | WO 2005/021063 A2 | 3/2005 |
| WO | WO 2005/032622 | 4/2005 |
| WO | WO 2005/034812 A1 | 4/2005 |
| WO | WO 2005/062980 A2 | 7/2005 |
| WO | WO 2005/063980 A1 | 7/2005 |
| WO | WO-2005/072654 A1 | 8/2005 |
| WO | WO 2006/066327 | 6/2006 |
| WO | WO-2006/066327 A1 | 6/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2007/047488 A2 | 4/2007 |
| WO | WO 2007/047945 A2 | 4/2007 |
| WO | WO 2007/059252 A1 | 5/2007 |
| WO | WO-2007/071436 A2 | 6/2007 |
| WO | WO 2007/120543 A1 | 10/2007 |
| WO | WO-2008/028569 A1 | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/101083 A2 | 8/2008 |

OTHER PUBLICATIONS

Translation of Aortenklappenbioprothese erfolgreich in der Entwicklung (2 pages).
Screen shots from http://www.fraunhofer.de/presse/filme/2006/index.jsp (2 pages), 2006.
Liang, Ma, et al., "Double-crowned valved stents for off-pump mitral valve replacement," European Journal of Cardio-Thoracic Surgery, 194-198 (5 pages), Jun. 13, 2005.
Huber, Christoph, et al. "Direct Access Valve Replacement (DAVR)—are we entering a new era in cardiac surgery?" European Journal of Cardio-Thoracic Surgery, 380-385, (6 pages), Jan. 19, 2006.
Extended European Search Report for Application No. 07116242.4-2310 dated Mar. 31, 2008 (10 pages).
File history for German Patent DE 195 46 692 filed Dec. 14, 1995 and patented Jul. 11, 2002.
International Search Report for PCT/US83/01932 corresponding to WO 84/02266.
C. Massimo & L. Boffi; "Myocardial, Revascularization by a New Method of Carrying Blood Directly From the Left Ventricular Cavity into the Coronary Circulation"; Journal of Thoracic Surgery; Aug. 1957; pp. 257-264; vol. 34; U.S.A.
Banning G. Lary & Roger W. Sherman; "A method for creating a coronary-myocardial artery"; Surgery; Jun. 1966; pp. 1061-1064; vol. 59, No. 6; The C.V. Mosby Company; St. Louis, MO.
Akio Wakayabashi, Solomon T. Little, Jr. & John E. Connolly; "Myocardial Boring for the Ischemic Heart"; Archives of Surgery; Nov. 1967; pp. 743-752; vol. 95; American Medical Asssociation; U.S.A.
Banning G. Lary, Antonio Camelo, Roger W. Sherman & Thomas J. Noto; "Myocardial Revascularization Experiments Using the Epicardium"; Archives of Surgery.; Jan. 1969; pp. 69-72; vol. 98; American Medical Association; U.S.A.
Ladislav Kuzela & George E. Miller, Jr.; "Experimental evaluation of direct transventricular revascularization"; Journal of Thoracic and Cardiovascular Surgery; Jun. 1969; pp. 770-773; vol. 57, No. 6; The C.V. Mosby Company; St. Louis, MO.

Ian Munro & Peter Allen; "The possibility of myocardial revascularization by creation of a left ventriculocoronary artery fistula"; The Journal of Thoracic and Cardiovascular Surgery; Jul. 1969; pp. 25-32; vol. 58, No. 1; The C.V. Mosby Company; St. Louis, MO.

Isam N. Anabtawi, Hubert F. Reigler, & Robert G. Ellison; "Experimental evaluation of myocardial tunnelization as a method of myocardial revascularization"; Journal of Thoracic and Cardiovascular Surgery; Nov. 1969; pp. 638-646; vol. 58, No. 5; The C.V. Mosby Company; St. Louis, MO.

L. Levinsky, T.Z. Lajos, A.B. Lee, Jr., C. Espersen, & G. Schimert; "The Revival of the Horseshoe Graft (Side-toSide Saphenous-Vein-to-Aorta Anastomosis"; The Thoracic and Cardiovascular Surgeon; Oct. 1979; pp. 322-324; vol. 27, No. 5; Georg Thieme Publishers; Stuttgart, Germany.

Garrett Lee, Richard M. Ikeda, Jerold Theis, Daniel Stobbe, Claire Ogata, Henry Lui, Robert L. Reis, & Dean T. Mason; "Effects of laser Irradiation delivered by flexible fiberoptic system on the left ventricular internal myocardium"; American Heart Journal; Sep. 1983; pp. 587-590; vol. 106, No. 3; The C.V. Mosby Company; St. Louis, MO.

Gerald Zemel, Barry T. Katzen, Gary J. Becker, James F. Benenati & D. Skip Sallee; "Percutaneous Transjugular Portosystemic Shunt"; The Journal of the American Medical Association; Jul. 1991; pp. 390-393; vol. 266, No. 3; American Medical Association; U.S.A.

Katherine S. Tweden, Frazier Eales, J. Douglas Cameron, Jerry C. Griffin, Eric E. Solien & Mark B. Knudson; "Ventriculocoronary Artery Bypass (VCAB), a Novel Approach to Myocardial Revascularization"; Feb. 2000; Article #2000-4653.

Mills, Noel L. et al., "Valvulotomy of valves in the saphenous vein graft before coronary artery bypass," The Journal of Thoracic and Cardiovascular Surgery, 71(6), pp. 878-879, Jun. 1976.

Baba et al., "Hemodynamic effects of venous valves in aorto-coronary bypass grafts," The Journal of Thoracic and Cardiovascular Surgery, 71(5), pp. 774-778, May 1976.

Phillips, Steven J. M.D. et al, "Improvement in Forward Coronary Blood Flow by Using a Reversed Saphenous Vein with a Competent Valve," The Annals of Thoracic Surgery, 21(1), pp. 12-15, Jan. 1976.

Anne Bohning, Kenneth Jochim & Louis N. Katz; "The Thebesian Vessels as a Source of Nourishment for the Myocardium"; American Journal of Physiology; 1933; pp. 183-200; vol. 106; American Physiological Society; U.S.A.

Alfred Goldman, Seymour M. Greenstone, Fred S. Preuss, Sherman H. Strauss & En-shu Chang; "Experimental Methods for Producing a Collateral Circulation to the Heart Directly from the Left Ventricle"; Journal of Thoracic Surgery; Mar. 1956; pp. 364-374; vol. 31, No. 3; U.S.A.

Banning G. Lary & Roger W. Sherman; "A method for creating a coronary-myocardial artery"; Surgery; Jun. 1966; pp. 1061-1064; vol. 59, No. 6; The C.V. Mosby Company; St. Louis, MO.

Julio C. Palmaz, Francisco Garcia, Randy R. Sibbitt, Fremin O. Tio, David T. Kopp, Wayne Schwesinger, Jack L. Lancaster & Peter Chang; "Expandable Intrahepatic Portacaval Shunt Stents in Dogs with Chronic Portal Hypertension"; American Journal of Roentgenology; Dec. 1986; pp. 1251-1254; vol. 147; The American Roentgen Ray Society; U.S.A.

Robert J. Gardner, Benjamin L. Plybon & Herbert E. Warden; "An Experimental Anatomic Study of Indirect Myocardial Revascularization"; Journal of Surgical Research; 1971; pp. 243-247; vol. 11; Academic Press; U.S.A.

Frank M. Galioto, Milton J. Reitman, Arnold J. Slovis & Irving A. Sarot; "Right coronary artery to left ventricle fistula: A case report and discussion"; American Heart Journal; Jul. 1971; pp. 93-97; vol. 82, No. 1; The C.V. Mosby Company; St. Louis, MO.

Joseph P. Archie Jr.; "Intramyocardial Pressure: Effect of Preload on Transmural Distribution of Systolic Coronary Blood Flow"; The American Journal of Cardiology; Jun. 1975; pp. 904-911; vol. 35; U.S.A.

S. Sultan Ahmed, Bunyad Haider & Timothy J. Regan; "Silent left coronary artery-cameral fistula: probable cause of myocardial ischemia"; American Heart Journal; Oct. 1982; pp. 869-870; vol. 104, No. 4, pt. 1; The C.V. Mosby Company; St. Louis, MO.

Julio C. Palmaz, Randy R. Sibbitt, Stewart R. Reuter, Francisco Garcia & Fremin O. Tio; "Expandable Intrahepatic Portacaval Shunt Stents: Early Experience in the Dog"; American Journal of Roentgenology; Oct. 1985; pp. 821-825; vol. 145; The American Roentgen Ray Society; U.S.A.

Goetz M. Richter, Gerd Noeldge, Julio C. Palmaz, Martin Roessle, Volker Slegerstetter, Martina Franke, Wolfgang Gerok, Werner Wenz & Edward Farthman; "Transjugular Intrahepatic Portacaval Stent Shunt: Preliminary Clinical Results"; Radiology; Mar. 1990; pp. 1027-1030; vol. 174, No. 3, Pt. 2; The Radiological Society of North America; Oak Brook, IL.

Medical Industry Today Headline News; "Eclipse Gets OK to Pump Catheter Marketing in Europe"; Jul. 17, 1998; pp. 1-2; Article #07179802, Article is 349 words long; Medical Data International, Inc.; Santa Ana, CA.

Medical Industry Today Headline News; "Sales Dive, Losses Soar in 2Q for CardioGenesis"; Jul. 17, 1998; pp. 1-2; Article #07179808, Article is 560 words long; Medical Data International, Inc.; U.S.A.

Howard A. Cohen & Marco Zenati; "Alternative Approaches to Coronary Revascularization"; Current International Cardiology Reports; 1999; pp. 138-146; vol. 1; Current Science, Inc.; U.S.A.

Stephen N. Oesterle, Nicolaus Reifart, Motoya Hayase, Eugen Haputmann, Reginald Low, Raimund Erbel, Michael Hause, Olaf Dirsch, Gerhard C. Schuler, Renu Virmani & Alan C. Yeung; "Catheter-Based Coronary Bypass: A Development Update"; Catheterization and Cardiovascular Interventions; 2003; pp. 212.218; vol. 58; Wiley-Liss, Inc.; U.S.A.

US 6,331,185, 12/2001, Gambale et al. (withdrawn)

* cited by examiner

METHODS AND CONDUITS FOR FLOWING BLOOD FROM A HEART CHAMBER TO A BLOOD VESSEL

CROSS-REFERENCE TO RELATED APPLICATION

This is a divisional application of U.S. application Ser. No. 10/928,190, filed Aug. 30, 2004, now U.S. Pat. No. 7,704,222 which is a continuation of U.S. application Ser. No. 09/828, 794, filed Apr. 10, 2001, now U.S. Pat. No. 6,881,199, which is a continuation of U.S. application Ser. No. 09/369,061, filed Aug. 4, 1999, now U.S. Pat. No. 6,254,564, which claims the benefit of U.S. Provisional Application Ser. No. 60/099, 719, filed Sep. 10, 1998, the entire disclosures of each being incorporated by reference herein.

FIELD OF THE INVENTION

This invention relates to apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations having a blood vessel graft incorporated therein for controlling the flow of blood through the conduit to achieve bypass of an occluded or stenosed coronary artery.

BACKGROUND OF THE INVENTION

Coronary artery disease is a major problem in the U.S. and throughout the world. Coronary arteries as well as other blood vessels frequently become clogged with plaque which, at the very least, can reduce blood and oxygen flow to the heart muscle (myocardium), and may impair the efficiency of the heart's pumping action, and can lead to heart attack (myocardial infarction) and death. In some cases, these coronary arteries can be unblocked through noninvasive techniques such as balloon angioplasty. In more difficult cases, a surgical bypass of the blocked vessel is necessary.

In a coronary bypass operation, one or more venous segments are inserted between the aorta and the coronary artery, or, alternatively, the distal end of an internal mammary artery is anastomosed to the coronary artery at a site distal to the stenosis or occlusion. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass graft (CABG) surgery, however, is a very intrusive procedure which is expensive, time-consuming, and traumatic to the patient. The operation requires an incision through the patient's sternum (sternotomy), and that the patient be placed on a heart-lung bypass pump so that the heart can be operated on while not beating. A saphenous vein graft is harvested from the patient's leg, another highly invasive procedure, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type or location of the blockage or stenosis, or due to the risk of emboli.

Thus, there is a need for an improved coronary bypass system which is less traumatic to the patient.

SUMMARY OF THE INVENTION

The present invention addresses the need in the previous technology by providing a coronary bypass system which avoids a sternotomy and other intrusive aspects associated with coronary bypass surgery. It also frees the surgeon from having to perform multiple anastomoses, as is necessary in the current process.

The present device provides a conduit for diverting blood directly from a heart chamber, such as the left ventricle of the heart, to the coronary artery distal to the blockage or stenosis, thereby bypassing the blocked portion of the vessel. The conduit comprises a tube adapted to be positioned in the heart wall and having a section of blood vessel attached to the interior of the conduit, to provide a passage for blood flow which is similar to the body's own blood vessels.

The conduit device is delivered through the coronary artery to a position distal the blockage or stenosis. At that position, the coronary artery and the wall of the left ventricle, including the myocardium, are pierced to provide an opening or channel completely through from the coronary artery to the left ventricle of the heart. The conduit is then positioned in the opening to provide a permanent passage for blood to flow between the left ventricle of the heart and the coronary artery, distal to the blockage or stenosis.

The conduit is sized so that one open end is positioned within the coronary artery, while the other open end is positioned in the left ventricle. Prior to implantation of the conduit, a section of vein or other blood vessel is obtained from the patient, from another human donor, or from a nonhuman animal. The vein or other blood vessel is sized so as to fit within the interior of the conduit. The hollow lumen of the conduit with the blood vessel graft inserted therein provides a passage for the flow of blood.

If desired, the section of blood vessel inserted into the conduit may include one or more naturally occurring one-way valves. The valve prevents the backflow of blood from the myocardium into the left ventricle. For example, a section of vein having a valve therein can be used. Alternatively, the pulmonic valve or aortic valve obtained from a nonhuman animal, such as a fetal pig or piglet, can be used to provide a one-way passage for the flow of blood through the conduit.

DETAILED DESCRIPTION OF THE PREFERRED EMBODIMENT

Figure 1A:
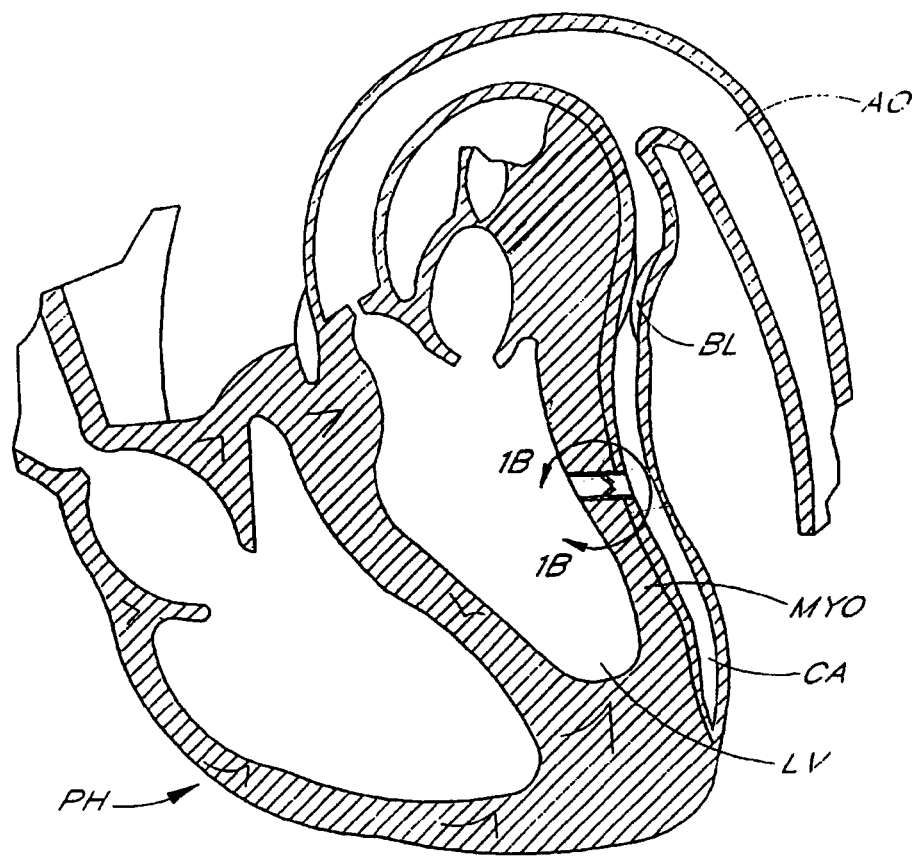
FIG. 1A is a schematic, cross-sectional view of a human heart, showing a conduit in the myocardium of the heart for forming a bypass between the left ventricle and a coronary artery.

As is well known, the coronary artery branches off the aorta and is positioned along the external surface of the heart wall.

Oxygenated blood that has returned from the lungs to the heart then flows from the heart to the aorta. Some blood in the aorta flows into the coronary arteries, and the remainder of blood in the aorta flows on to the rest of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

As used herein, the term "heart chamber" primarily refers to the interior, or lumenal, aspect of the left or right ventricle or the left or right atrium. The term "conduit," "stent," and "tube" herein refer to physical structures, preferably primarily artificial, that can be positioned between two or more chambers or vessels, to allow blood flow from one chamber or vessel to another. A "shunt" is any natural or artificial passage between natural channels, such as heart chambers or blood vessels. The conduit in the preferred arrangement can be made of a variety of materials, including various metals, such as nitinol, or plastics.

As used herein, the term "heart wall" comprises any one or more of the following portions or layers of the mammalian heart: the epicardium, myocardium, endocardium, pericardium, interatrial septum, and interventricular septum.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "tansmyocardial" should not be narrowly construed in connection with the preferred fluid communication conduits, and other nonmyocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the obstructions that are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In order to restore the flow of oxygenated blood through the coronary artery, the preferred arrangement provides for the shunting of blood directly from the heart to a site in the coronary artery which is distal the blockage or stenosis.

Although the specification herein will describe the conduit primarily with reference to the left ventricle, the preferred arrangement can be used with any of the four heart chambers, and with any coronary artery, including the left main coronary artery, the right coronary artery, the left anterior descending artery, the left circumflex artery, the posterior descending artery, the obtuse marginal branch or a diagonal branch.

A tunnel or opening is formed through the wall of the coronary artery and the myocardium and into the left ventricle of the heart which lies beneath, or deep to, the coronary artery. A conduit is positioned in the opening to keep it open.

The conduit may be introduced into the myocardium in a variety of ways, including by a catheter threaded through the femoral artery into the aorta and thence into the left ventricle and, if necessary, the left atrium; or by a catheter threaded through the femoral vein into the inferior vena cava and thence into the right atrium and right ventricle. Alternatively, the conduit may be introduced through a surgical incision in chest wall (thoracotomy) or sternum (sternotomy).

Further details regarding conduits and conduit delivery systems are described in patent applications entitled DESIGNS FOR LEFT VENTRICULAR CONDUIT U.S. application Ser. No. 09/369,048, filed Aug. 4, 1999, VALVE DESIGNS FOR LEFT VENTRICULAR CONDUIT U.S. application Ser. No. 09/368,393, filed Aug. 4, 1999, LEFT VENTRICULAR CONDUITS TO CORONARY ARTERIES AND METHODS FOR CORONARY BYPASS, U.S. application Ser. No. 09/534,038, filed Mar. 24, 2000, and BLOOD FLOW CONDUIT DELIVERY SYSTEM AND METHOD OF USE, U.S. application Ser. No. 09/368,644, filed Aug. 4, 1999, and U.S. Pat. Nos. 6,261,304, 5,429,144 and 5,662,124, the disclosures of which are all hereby incorporated by reference in their entirety.

The opening through the heart wall (including endocardium, myocardium, and epicardium) and coronary artery can be formed in a variety of ways, including by knife or scalpel, electrocautery, cryoablation, radiofrequency ablation, ultrasonic ablation, and the like. Other methods will be apparent to those of ordinary skill in the art.

The conduit is provided with a section of vein or other blood vessel positioned within its interior lumen. The section of vein or other blood vessel is obtained from the patient, from a donor, or from an animal. Prior to implantation of the conduit, a segment of blood vessel sized to fit with the lumen of the conduit is inserted into the conduit. The conduit with the graft therein provides a passage for the flow of blood which is similar to the natural human blood vessels. The segment of vein or other blood vessel harvested to fit within the conduit may include one or more of the valves which naturally occur in the human body. These valves act to prevent the backflow of blood. In the conduit, these naturally occurring venous valves prevent the blood from flowing back into the left ventricle of the heart from the coronary artery. The segment of vein is preferably inserted into the conduit prior to the conduit's deployment into the human body by any of various surgical or catheter-guided techniques known to those of skill in the art.

Figure 1B:
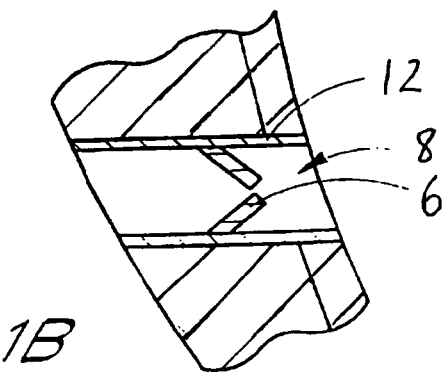
FIG. 1B is an enlarged view of the bypass conduit of FIG. 1A.

Referring now to FIGS. 1A and 1B, a coronary artery bypass is accomplished by disposing a conduit 12 (FIG. 1B) in a heart wall or myocardium MYO of a patient's heart PH (FIG. 1A). The conduit 12 preferably extends from the left ventricle LV of heart PH to a clogged coronary artery CA at a point downstream of a blockage BL to create a passageway 8 therethrough. Conduit 12 is preferably made of a biocompatible material such as stainless steel or nitinol although other materials such as Ti, Ti alloys, Ni alloys, Co alloys and biocompatible polymers may also be used. In one embodiment, conduit 12 has a one way valve 6 to allow blood to flow from the left ventricle LV to the coronary artery CA. Although the conduit 12 may elastically deform under the contractive pressure of the heart muscle during systole, the stent remains open to allow blood to pass from the patient's left ventricle LV into the coronary artery CA. During diastole, the blood pumped into coronary artery through passageway 8 is blocked by one-way valve 6 from returning to left ventricle LV.

Figure 2:
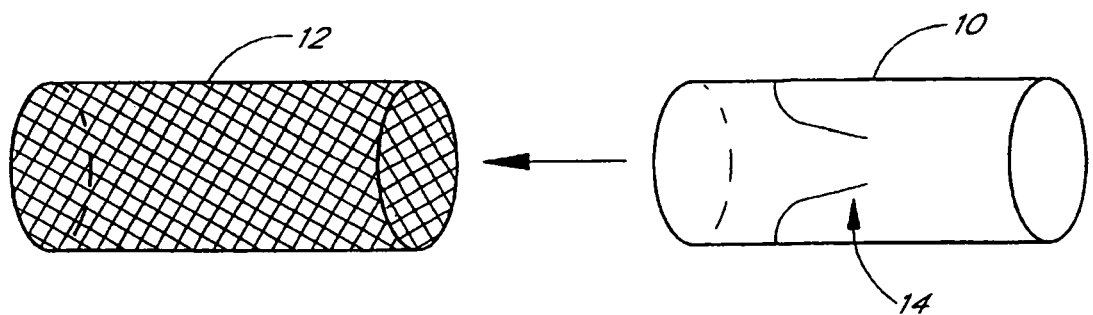
FIG. 2 is an exploded view of a vein graft incorporated into a heart conduit in accordance with the preferred arrangement.

As shown in FIG. 2, a preferred embodiment involves the use of a vein graft 10 taken from the patient. Prior to preparing the conduit 12 for placement in the patient, a section of vein 10 is obtained from the patient (i.e., an autologous graft or autograft). Of course, a blood vessel taken from another human donor (i.e., an allogeneic graft or allograft) or nonhuman animal species (i.e., a heterologous graft or xenograft) could also be used. The vein 10 is preferably taken from the saphenous vein in the leg of the patient. Alternatively, a donor vein could be used, or a fetal pig or piglet can be obtained and dissected to remove a section of the pulmonary artery having a pulmonic valve therein, or a section of the aorta having an aortic valve therein, or a similar vessel having a naturally occurring valve system. In other embodiments, the endothelial lining of a vein and/or a valve may be grown from one or more tissue cultures, utilizing cloning of donor cell lines or other genetic engineering techniques (or "tissue engineering") known to those of skill in the art. Thus, as used herein, "a section of blood vessel" may include one or more of the following: a surgically resected segment of a blood vessel, with or without one or more valves; the endothelial lining of a blood vessel, taken from an in vitro or in vivo specimen; and one or more venous valves, taken from in vitro or in vivo specimens.

As noted above, the section of vein 10 or other blood vessel harvested preferably contains one or more valves 14, which occur naturally in the veins. The section of vein 10 may also not have a valve. The vein section 10 is sized so as to be the same length as the conduit 12. The vein section 10 is placed within the interior lumen of the conduit 12 and attached to the inside of the conduit 12 by suturing or other attachment methods. The natural vein graft 10 is biocompatible and therefore reduces problems associated with rejection of the conduit 12 and clotting around or in the conduit 12. In addition, the vein 10 provides a natural valve system 14 that is already used throughout the human body to prevent the backflow of blood. In the case of a xenograft, treatment of the graft with chemicals, such as glutaraldehyde, may be undertaken to remove living cells, including antigenic materials, from the connective tissue framework of the graft so as to reduce thrombogenicity and antigenicity.

Figure 3:
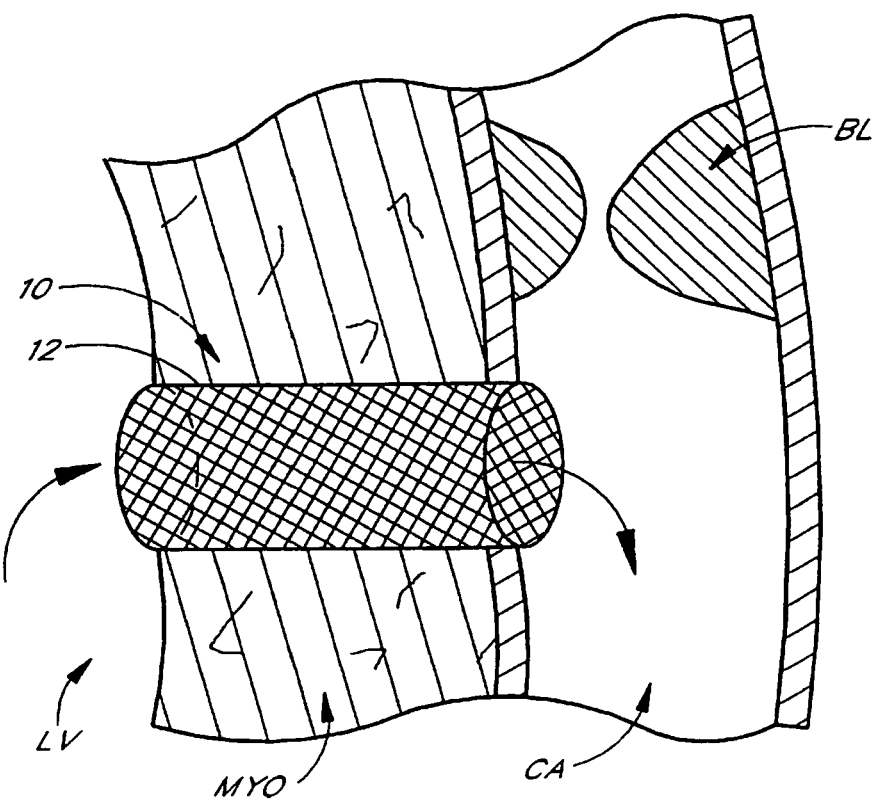
FIG. 3 is a close-up, cross-sectional view of a blockage or stenosis in the coronary artery, illustrating the conduit of the preferred arrangement positioned so as to bypass the blockage or stenosis.

Referring now to FIG. 3, a self-expanding conduit 12 having a section of vein 10 therein is introduced into the wall of the myocardium MYO as follows. A conduit delivery catheter (not shown), having the compressed conduit 12 mounted on its distal end, is advanced over a puncture mechanism and into the wall of the myocardium MYO at a site distal to the blockage or stenosis BL in the coronary artery CA. When the conduit 12 is property seated in the myocardial wall MYO, its retaining sheath is withdrawn, allowing the conduit 12 to expand and open a passageway, or maintain patency of the passageway, from the left ventricle of the heart LV to the coronary artery CA. This allows oxygenated blood to flow directly from the left ventricle of the heart LV through the conduit 12 and to the coronary artery CA, bypassing the section of coronary artery CA that is blocked BL, as shown by the arrows in FIG. 3.

The conduit 12 may include attachment mechanisms not limited to hooks, barbs large collars, and/or other methods to ensure that a seal is created between the coronary artery CA and the wall of the heart wall MYO, to prevent hemorrhaging and to prevent the threat of or actual conduit migration. When positioning and securing of the conduit 12 is completed, the remaining catheter assembly is removed, leaving the conduit 12 with the vein graft therein, in place in the body The present vascular conduit having a blood vessel graft incorporated therein provides significant improvements in the present treatment of blockages or stenoses in the coronary artery. Although the invention has been described in its preferred embodiments in connection with the particular figures, it is not intended that this description should be limited in any way by the foregoing.

What is claimed is:

1. A method of flowing blood from a left ventricle to an arterial blood-containing vessel, the method comprising:
   placing a conduit adjacent the left ventricle and the arterial blood-containing vessel such that upon implantation of the conduit a first end of the conduit is continuously open towards the left ventricle, a second end of the conduit is continuously open towards and positioned in the arterial blood-containing vessel, and at least a portion of the first open end faces at least a portion of the second open end, wherein the conduit has a substantially lattice structure adjacent each of the first and second ends and extending therebetween; and
   during diastole, restricting a flow of blood from the arterial blood-containing vessel to the left ventricle via a valve attached to the conduit within an interior of the conduit between the first and second ends.

2. The method of claim 1, further including enlarging an opening between the left ventricle and the arterial blood-containing vessel and placing the conduit within the opening after enlarging the opening.

3. The method of claim 1, further including inhibiting migration of the conduit via at least one of a hook, a barb, or a collar of the conduit.

4. The method of claim 1, further including placing the conduit onto a catheter so that the conduit is in a compressed state, and introducing the catheter into an aorta.

5. The method of claim 1, wherein the valve is an aortic valve.

6. The method of claim 1, wherein the valve is formed from tissue engineering techniques.

7. The method of claim 1, wherein the valve is obtained from a nonhuman animal.

8. The method of claim 1, wherein the first end is a distalmost end of the conduit and the second end is a proximalmost end of the conduit.

9. The method of claim 8, wherein each of the distalmost and the proximalmost ends is expandable.

10. The method of claim 1, wherein the first end of the conduit is positioned in the left ventricle.

11. The method of claim 1, wherein the conduit is a metal conduit.

12. The method of claim 1, wherein the conduit includes a longitudinal axis that is substantially straight between the first and second ends.

13. The method of claim 1, wherein a section of tissue is further attached within the interior of the conduit adjacent the first end.

14. A method of flowing blood from a left ventricle to an arterial blood-containing vessel, the method comprising:

placing a conduit adjacent the left ventricle and the arterial blood-containing vessel such that a first end of the conduit is continuously open towards the left ventricle and a second end of the conduit is continuously open towards and positioned in the arterial blood-containing vessel, wherein the conduit includes a longitudinal axis that is substantially straight between the first and second ends and wherein the conduit includes a substantially lattice structure adjacent each of the first and second ends and extending therebetween; and during diastole, restricting a flow of blood from the vessel to the left ventricle via a valve attached to the conduit within an interior of the conduit between the first and second ends.

15. The method of claim 14, further including enlarging an opening between the left ventricle and the arterial blood-containing vessel and placing the conduit within the opening after enlarging the opening.

16. The method of claim 14, further including inhibiting migration of the conduit via at least one of a hook, a barb, or a collar of the conduit.

17. The method of claim 14, further including placing the conduit onto a catheter so that the conduit is in a compressed state, and introducing the catheter into an aorta.

18. The method of claim 14, wherein the valve is an aortic valve.

19. The method of claim 14, wherein the valve is formed from tissue engineering techniques.

20. The method of claim 14, wherein the valve is obtained from a nonhuman animal.

21. The method of claim 14, wherein the first end is a distalmost end of the conduit and the second end is a proximalmost end of the conduit.

22. The method of claim 21, wherein each of the distalmost and the proximalmost ends is expandable.

23. The method of claim 14, wherein the first end of the conduit is positioned in the left ventricle.

24. The method of claim 14, wherein the conduit is a metal conduit.

25. A method of flowing blood from a left ventricle to an arterial blood-containing vessel, the method comprising:

placing a metal conduit adjacent the left ventricle and the arterial blood-containing vessel such that a first end of the conduit is continuously open towards the left ventricle, a second end of the conduit is continuously open towards and positioned in the arterial blood-containing vessel, and a substantially straight line intersects at least a portion of the first end and at least a portion of the second end; and during diastole, restricting a flow of blood from the arterial blood-containing vessel to the left ventricle via a tissue valve attached within an interior of the conduit such that the tissue valve is between the first and second ends, wherein a section of tissue is further attached within the interior of the conduit adjacent the first end.

26. The method of claim 25, further including enlarging an opening between the left ventricle and the arterial blood-containing vessel and placing the conduit within the opening after enlarging the opening.

27. The method of claim 25, further comprising inhibiting migration of the conduit via at least one of a hook, a barb, or a collar of the conduit.

28. The method of claim 25, further including placing the conduit onto a catheter so that the conduit is in a compressed state, and introducing the catheter into an aorta.

29. The method of claim 25, wherein the tissue valve is an aortic valve.

30. The method of claim 25, wherein the tissue valve is not a naturally occurring valve.

31. The method of claim 25, wherein the tissue valve is formed from tissue engineering techniques.

32. The method of claim 25, wherein the tissue valve is obtained from a nonhuman animal.

33. The method of claim 25, wherein the first end is a distalmost end of the conduit and the second end is a proximalmost end of the conduit.

34. The method of claim 33, wherein each of the distalmost and the proximalmost ends is expandable.

35. The method of claim 25, wherein the conduit includes a longitudinal axis and the first and second ends intersect the longitudinal axis.

36. The method of claim 25, wherein the first end of the conduit is positioned in the left ventricle.

37. The method of claim 36, further including enlarging an opening between the left ventricle and the arterial blood-containing vessel and placing the conduit within the opening after enlarging the opening.

38. The method of claim 36, further including inhibiting migration of the conduit via at least one of a hook, a barb, or a collar of the conduit.

39. The method of claim 36, further including placing the conduit onto a catheter so that the conduit is in a compressed state and introducing the catheter into the aorta.

40. The method of claim 36, wherein the tissue valve is an aortic valve.

41. The method of claim 36, wherein the tissue valve is not a naturally occurring valve.

42. The method of claim 36, wherein the tissue valve is formed from tissue engineering techniques.

43. The method of claim 36, wherein the tissue valve is obtained from a nonhuman animal.

44. The method of claim 36, wherein the first end is a distalmost end of the conduit and the second end is a proximalmost end of the conduit.

45. The method of claim 44, wherein each of the distalmost and the proximalmost ends is expandable.

46. The method of claim 36, wherein the conduit includes a longitudinal axis and the first and second ends intersect the longitudinal axis.

47. A method of flowing blood from a left ventricle to an arterial blood-containing vessel, the method comprising:

placing a metal conduit adjacent the left ventricle and the arterial blood-containing vessel, such that upon implantation of the conduit a first end of the conduit is continuously open towards the left ventricle and the a second end of the conduit is continuously open towards and positioned in the arterial blood-containing vessel, wherein the conduit includes a longitudinal axis that is substantially straight between the first and second ends;

during systolic contraction of the left ventricle, permitting oxygenated blood to flow from the left ventricle to the arterial blood-containing vessel; and during diastole, restricting a flow of blood from the arterial blood-containing vessel to the left ventricle via a tissue valve attached within an interior of the conduit such that the tissue valve is between the first and second ends, wherein a section of tissue is further attached within the interior of the conduit adjacent the first end.

48. The method of claim 47, wherein the first end of the conduit is positioned in the left ventricle.

* * * * *